United States Patent [19]

Cattani

[11] Patent Number: 4,684,345

[45] Date of Patent: Aug. 4, 1987

[54] SPITTLE SEPARATION AND DISPOSAL DEVICE INCORPORATING A DRAINAGE PUMP, IN PARTICULAR FOR SUCTION EQUIPMENT USED IN DENTISTRY

[75] Inventor: Augusto Cattani, Parma, Italy

[73] Assignee: Officine Augusto Cattani & C.S.p.A., Italy

[21] Appl. No.: 821,613

[22] Filed: Jan. 23, 1986

[30] Foreign Application Priority Data

Jul. 31, 1985 [IT] Italy ................... 40079 A/85

[51] Int. Cl.[4] .......................................... A61C 17/04
[52] U.S. Cl. ........................................ 433/92; 55/164; 55/421; 55/464
[58] Field of Search ................. 433/92; 55/164, 421, 55/215, 464

[56] References Cited

U.S. PATENT DOCUMENTS

| | | | |
|---|---|---|---|
| 680,717 | 8/1901 | Labadie | 55/464 |
| 873,336 | 12/1907 | Angell | 55/464 |
| 1,534,833 | 4/1925 | Binks | 55/464 |
| 1,816,871 | 8/1931 | Remington | 55/464 |
| 3,286,444 | 11/1966 | Boswinkle et al. | 55/215 |
| 3,746,033 | 7/1973 | Keiper | 433/92 |
| 3,988,134 | 10/1976 | Gandrud | 433/92 |
| 4,293,300 | 10/1981 | Cattani | 433/92 |
| 4,564,374 | 1/1986 | Hofmann | 433/92 |

FOREIGN PATENT DOCUMENTS 0023036  1/1981  European Pat. Off. ............. 433/92

*Primary Examiner*—John J. Wilson
*Attorney, Agent, or Firm*—Darby & Darby

[57] ABSTRACT

A spittle separation and disposal device is disclosed that incorporates a drainage pump and forms part of the suction equipment used in dentistry. The device comprises a separator vessel (1) fitted with a drain valve (2); the drainage pump (8), located downstream of the valve and kept normally at standstill, is set in motion by a control signal from level sensors (9, 10) within the vessel, whenever liquid in the vessel itself rises to a prescribed level. The vessel has a lid (3) provided with an element (14) in the form of a cone frustum the inside of which communicates with a port connected to an air pump, and the internal surface of which exhibits a number of helical starts (15) disposed in opposition to the helical pattern tern of movement of the air which is drawn up through the element by the air pump.

7 Claims, 2 Drawing Figures

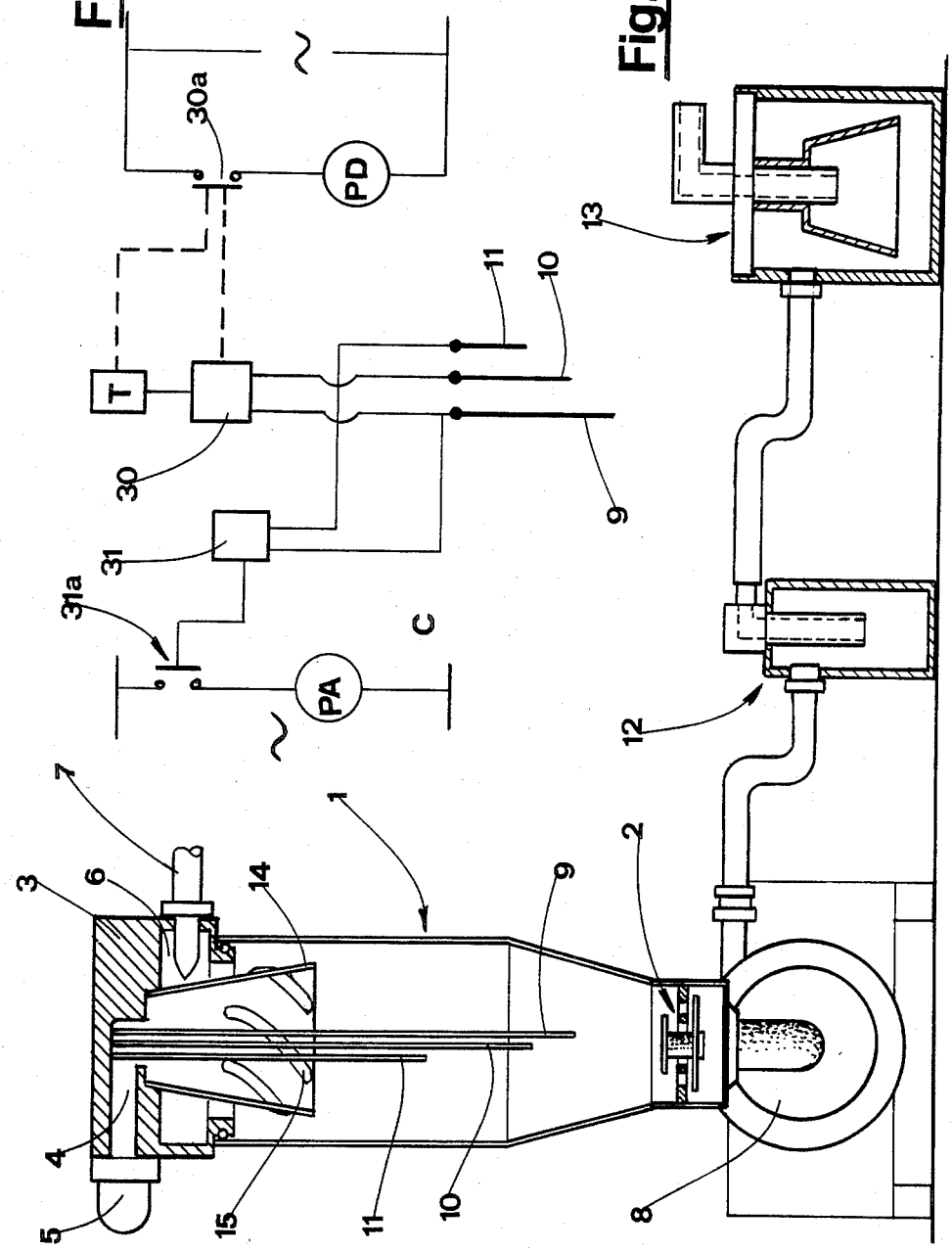

_4,684,345_

SPITTLE SEPARATION AND DISPOSAL DEVICE INCORPORATING A DRAINAGE PUMP, IN PARTICULAR FOR SUCTION EQUIPMENT USED IN DENTISTRY

BACKGROUND OF THE INVENTION

The invention described herein relates to a spittle separation and disposal device, which incorporates a drainage pump, and constitutes part of the suction equipment used in dental treatment.

In many instances, suction equipment of the type used in dentistry for removing liquid and debris (spittle, for convenience) from the mouth of a patient during treatment, comprises a separator vessel inside which partial vacuum conditions are created, by an air pump for example; spittle is extracted from the patient's mouth by a tube which connects with this vessel and discharges directly thereinto. Such liquids as are drawn in will then be emptied from the vessel, say, into the sewer.

As concerning extraction of the liquids from such a vessel, the prior art embraces methods that include the use of a drainage pump which is designed to take in liquids from the separator vessel at a negative pressure (the partial vacuum aforementioned) and discharge them in ambient conditions, into the sewer for instance, at atmospheric pressure.

Drainage pumps in prior art devices take in liquid continuously from the separator vessel, and become the source of considerable servicing problems as a result, by reason of their running empty too often; such is inevitably the condition whenever the equipment is started up, and the same condition recurs not infrequently during normal operation due to those periods, of greater or less duration, when intake of liquid from the vessel is either low, or altogether non-existent The effect on the drainage pump of running empty is that it overheats, and the seals suffer damage.

Another defect which occurs in prior art devices is that foam, or droplets of liquid, extracted from the patient's mouth through the tube and discharged into the separate vessel, can work their way up the tube and foul the air pump, with the result that this pump too suffers damage.

It is an object of the invention disclosed to overcome such drawbacks, providing a spittle separation and disposal device in which the possibility of damage to the drainage pump is reduced to a minimum, and in which backflow of foam and droplets through the suction tube is rendered practically impossible.

It is a further object of the invention to provide a spittle separation and disposal device the operation of which is simple and dependable in the extreme.

One advantage of the spittle separation and disposal device disclosed is that it will permit of eliminating solid matter from the liquids ultimately discharged into the sewer.

A further advantage of the device is that suction remains uninterrupted during normal operation; what is more, the use of a drainage pump ensures disposal of foam, which cannot be achieved with a separator where no such pump is employed.

SUMMARY OF THE INVENTION

The stated objects and advantages are realized with a device as claimed hereinafter: a device, that is, of a general type comprising a separator vessel provided with a drain valve which remains normally open at atmospheric pressure, and enclosed uppermost by a lid having a first port to which an air pump is connected and a second port to which one or more tubes are connected, directly or indirectly, for the extraction of spittle from the mouth of the patient; and a drainage pump located downstream of the drain valve, serving to dispose of the liquid contents of the separator vessel.

In the device disclosed, the drainage pump remains normally at standstill, and is set in motion by start-control means whenever the liquid contents of the separator vessel rise to a prescribed level; first stop-control means relay a signal occasioning shut-off of the drainage pump whenever the liquid contents of the vessel fall below the same prescribed level. A timer is also employed by means of which to keep the drainage pump running for a given length of time following relay of the shut-off signal.

BRIEF DESCRIPTION OF THE DRAWINGS

A preferred embodiment of the invention will now be described in detail, by way of example, with the aid of the accompanying drawings, in which:

FIG. 1 is a section through the device, viewed in vertical elevation;

FIG. 2 shows the diagram of a possible circuit interconnecting the various components of the device.

DESCRIPTION OF THE PREFERRED EMBODIMENT

The device disclosed comprises a separator vessel 1 of substantially cylindrical shape, the bottom end of which tapers toward a drain valve 2; the valve is a poppet type, and remains normally open at atmospheric pressure—i.e. when the device is not in operation.

The vessel 1 is provided with a lid 3 having a first port 4 that is connected, by way of a first suction line 5, with an air pump (not illustrated in FIG. 1), and a second port 6 connected via a second suction line 7 with a tube, or, where more than one such tube is utilized, with the manifold of a dentist's console of conventional type, into which spittle drawn in by the various tubes is channeled.

The lid 3 is provided with an element in the form of a cone frustum, denoted 14, the greater base of which is located within the vessel 1, the smaller base connecting with the first port 4. The internal surface of the cone 14 exhibits a plurality of helical starts 15 disposed in opposition to the helical pattern of movement of air which is drawn up and out by way of the first port 4 into the first suction line. The function of such helical starts 15 is essentially one of impeding the flow of foam or droplets up into the cone 14 thereby ensuring that the first suction line, hence the air pump, draws in air only. The geometrical arrangement of the helical starts 15 cancels out, or at all events, minimizes the upward entrainment of liquid particles such that these particles arrive no further than the lower lip of the cone 14.

8 denotes a drainage pump located downstream of the drain valve 2, the function of which is to draw off liquid from the vessel.

Downstream of the pump 8, one has a liquid reservoir, embodied as a first trap 12 consisting of two concentric cylindrical elements, and further downstream, a second trap 14 likewise consisting of two concentric cylindrical elements; the cylindrical elements of the second trap 13 are of greater diameter than those of the first trap 12, for reasons which will become apparent in due course: e.g., were the outer cylinder of the first trap to measure 01 or 1½" approx, then that of the second trap would measure 03-3½" approx.

9, 10 and 11 denote respective first, second and third level sensors of conventional type located within the vessel 1, the leads of which are routed out by way of the lid 3. The first and second sensors 9 and 10 constitute start-control means which, by providing an electrical control signal, will set the drainage pump in motion whenever jointly immersed by liquid or by foam in the vessel, the level of which must rise, clearly enough, to the level at which the sensors are positioned. These same two sensors 9 and 10 constitute first stop-control means the function of which is to relay a control signal occasioning shut-off of the drainage pump; it will be similarly clear that such a signal remains active as long as the level of liquid in the vessel remains below that of the sensors. With this shut-off control signal relayed to the pump, a timer cuts in and allows the pump to continue running for a given period following receipt of the signal; such a delay provided by the timer will generally be brief, say, of the order of 2 to 5 seconds, and calculated to ensure disposal of such liquid as remains in the vessel at the moment of relaying the shut-off signal.

The first sensor 9 and the third sensor 11 together constitute second stop-control means designed to relay an electrical signal that causes operation of the air pump to cease whenever liquid in the vessel rises to a given level; naturally enough, this level will be higher than that which triggers the control means governing operation of the drainage pump. Such second stop-control means provide a safety feature that prevents the level of liquid rising to the point where droplets or foam might be drawn into the air suction line 5, for example, in circumstances where inordinately large quantities of spittle are drawn into the separator. Even with the air pump at standstill, the drainage pump continues to operate (the first and second sensors 9 and 10 remaining immersed) until the greater part of the liquid contents is disposed of. Whilst it is true that the liquid could be drained off gravitationally through the drain valve with the air pump shut off, the drainage pump is kept running nonetheless, so as to avoid gurgling of air within the vessel, and ensure troublefree, swift disposal of the liquid contents.

FIG. 2 illustrates a possible circuit, by way of example, connecting the sensors with drive systems of the drainage pump (PD), and the air pump (PA), in such a way as to produce the effects and control signals aforedescribed. T denotes the timer, and 30 & 31 are blocks of conventional circuitry which process the signals supplied by the sensors and gate the make or break configurations at respective contacts 30a and 31a accordingly.

Operation of the device is as follows: with the air pump at standstill, pressure within the vessel remains at atmospheric level and the suction tubes draw in nothing; in these conditions, the drain valve remains open, and the vessel connects by way of the drainage pump (likewise at standstill) and its relative outlet, with the first trap.

Setting the air pump in motion by way of an external control, air is extracted from the vessel, and pressure gradually drops therein; this pressure drop in turn causes a part of the liquid in the first trap to be drawn back into the drainage pump, which is motionless since as yet the vessel contains no liquid to trigger the first and second sensors 9 and 10.

The gradual creation of a partial vacuum in the vessel ultimately causes the drain valve to close with the result that the suction tubes, connected now with a source of negative pressure, begin drawing in spittle from the mouth of the patient.

Spittle drawn in through the suction tubes enters the vessel 1 by way of the second port 6, and the level of the liquid contents rises gradually in the vessel. As long as the level of the liquid remains below that of the first and second sensors 9 and 10, the drainage pump will remain motionless; on arrival of the liquid at the prescribed level, the electrical contact gated by immersion of the sensors duly starts up the drainage pump drive motor. It will be recalled that liquid is drawn back from the first trap by the initial drop in pressure; the drainage pump is therefore filled with liquid and started up each time in a primed condition, thus avoiding any damage whatever to its component parts.

With the drainage pump now set in motion, the drain valve opens, whereupon the liquid contents of the vessel are drawn off by the pump and discharged by way of the first and second traps into the sewer. This gradual disposal of the liquid contents causes their level to drop within the vessel 1; on arrival at the point where the first sensor 9 and the second sensor 10, and particularly the second sensor, are left dry, the signal is gated which instructs a break in the contact governing operation of the drainage pump.

In practice, the timer permits further operation of the pump for a short space of time so that the liquid remaining within the vessel can be fully disposed of; the delay effectively produced by the timer will be calculated, at all events, to ensure that the drainage pump will never start up without being primed.

With the delay provided by the timer duly elapsed, the drainage pump shuts off and the cycle repeats.

In the event that the flow of liquid taken into the vessel outstrips the disposal flow rate of which the drainage pump is capable, or in other words, in those rare instances where the level of the liquid contents of the vessel continues to rise even with the drainage pump in operation, ultimate immersion of the third sensor 11 will also shut off the air pump; in this state, the device ceases operation altogether, except for the drainage pump, which continues to dispose of the vessel's liquid contents.

Once the vessel 1 is emptied completely of its liquid contents, the air pump is reset manually, It will be noted that, even following shut-off and subsequent emptying of the device, the first trap 12 remains full of liquid; thus, when the device is next started up, a backflow of liquid will occur from the trap 12 into the drainage pump, as described beforehand, and any possibility of the pump's running empty is duly avoided.

To a certain extent, the first trap 12 also performs a sedimentation role, in that the more consistent of solid matter contained in the waste liquid will be deposited at the bottom of the outer cylinder. A much more effective sedimentation is brought about in the second trap 13 however, which retains solid particles of miniscule dimensions and thus prevents their being discharged into the sewer. More exactly, velocity of the flow of waste through the bottom part of the inner cylinder of this second trap 13 is considerably less than through the top part of the self-same inner cylinder, since the section of the bottom part is noticeably larger than that of the top part.

The two waste traps will be opened up from time to time (less frequency in the case of the first 12) in order to empty out such solids as have settled.

What is claimed:

1. A spittle separation and disposal device incorporating a drainage pump, in particular for suction equipment used in dentistry, comprising a separator vessel (1), provided with a drain valve (2) which remains normally open at atmospheric pressure, and enclosed uppermost by a lid (3) having a first port (4) to which an air pump is connected and a second port (6) to which one or more tubes are connected, directly or indirectly, for the extraction of spittle from the mouth of the patient; and a drainage pump (8) located downstream of the drain valve that serves to dispose of the liquid contents of the separator vessel; wherein the drainage pump, which remains normally at standstill, is set in motion by start-control means whenever the liquid contents of the separator vessel rise to a prescribed level, and shut off by first stop-control means that relay a signal whenever the liquid contents of the vessel fall below the same prescribed level; and wherein a timer is employed by means of which to keep the drainage pump running for a given length of time following relay of the shutoff signal.

2. Device as in claim 1 wherein the start-control means and the first stop-control means consist of a pair of conventional level sensors (9, 10) set at dissimilar heights and designed to relay an electrical 'make' or 'break' signal according to their joint immersed or non-immersed condition.

3. Device as in claim 1 wherein use is made of second stop-control means which are designed to shut off the air pump whenever the level of the liquid contents of the separator vessel rise to a prescribed level, and wherein the prescribed level in question is higher than the prescribed level which triggers the start-control means.

4. Device as in claim 3 wherein the second stopcontrol means consist of a pair of conventional level sensors (9, 11) designed to relay an electrical control signal when jointly immersed.

5. A device as in claim 1, comprising a liquid reservoir embodied as a first trap (12) consisting of two concentric cylindrical elements, and a second trap (13) consisting of two concentric cylindrical elements the respective diameters of which are greater than those of the first trap, wherein the first trap is located downstream of the drainage pump, and the second trap is located downstream of the first trap.

6. Device as in claim 5, wherein the bottom part of the inner cylindrical element of the second trap is of greater diameter than the top part thereof.

7. Device as in claim 1 wherein the lid is provided with an element (14) having the form of a cone frustum, the greater base of which is located within the vessel, and the smaller base of which connects with the first port; and wherein the internal surface of such an element exhibits a plurality of helical starts (15) disposed in opposition to the helical pattern of movement of air drawn up through the element itself.

* * * * *